(12) United States Patent
Scheiner et al.

(10) Patent No.: US 9,032,956 B2
(45) Date of Patent: *May 19, 2015

(54) CUSHION FOR MASK SYSTEM

(71) Applicant: ResMed Limited, Bella Vista (AU)

(72) Inventors: Rupert Christian Scheiner, Davidson (AU); Scott Alexander Howard, Harbord (AU); Gregory Scott Smart, Randwick (AU); Christopher Scott Skipper, North Ryde (AU); Steven John Lubke, Stanmore (AU); Timothy Shawn Nelson, Marrickville (AU)

(73) Assignee: ResMed Limited, Bella Vista (AU)

( * ) Notice: Subject to any disclaimer, the term of this patent is extended or adjusted under 35 U.S.C. 154(b) by 134 days.

This patent is subject to a terminal disclaimer.

(21) Appl. No.: 13/803,787

(22) Filed: Mar. 14, 2013

(65) Prior Publication Data

US 2013/0239973 A1 Sep. 19, 2013

Related U.S. Application Data

(63) Continuation of application No. 12/311,489, filed as application No. PCT/AU2007/001456 on Oct. 2, 2007, now Pat. No. 8,402,971.

(60) Provisional application No. 60/848,360, filed on Oct. 2, 2006.

(51) Int. Cl.
*A61M 16/06* (2006.01)

(52) U.S. Cl.
CPC ............ *A61M 16/06* (2013.01); *A61M 16/0666* (2013.01); *A61M 16/0683* (2013.01); *A61M 2205/6045* (2013.01); *A61M 2210/0625* (2013.01); *A61M 16/0616* (2014.02); *A61M 16/0622* (2014.02); *A61M 16/0611* (2014.02)

(58) Field of Classification Search
CPC ............ A61M 16/06; A61M 16/0616; A61M 16/0622; A61M 16/0666; A61M 16/0611; A61M 2205/6045; A61M 2210/0625; A61M 16/0683
USPC ............................. 128/206.24, 201.24, 207.11
See application file for complete search history.

(56) References Cited

U.S. PATENT DOCUMENTS

| | | | |
|---|---|---|---|
| 5,349,949 A | 9/1994 | Schegerin | |
| 8,402,971 B2 * | 3/2013 | Scheiner et al. | 128/206.24 |
| 2006/0283461 A1 | 12/2006 | Lubke et al. | |
| 2011/0056497 A1 | 3/2011 | Scheiner et al. | |

FOREIGN PATENT DOCUMENTS

| | | |
|---|---|---|
| EP | 1 258 266 | 11/2002 |
| FR | 2 823 122 | 10/2002 |
| WO | WO 2004/022146 | 3/2004 |
| WO | PCT/AU2006/000032 | 1/2006 |
| WO | WO 2006/130903 | 12/2006 |

OTHER PUBLICATIONS

International Search Report for PCT/AU2007/001456 (Dec. 12, 2007) (4 pages).

* cited by examiner

*Primary Examiner* — Manuel Mendez
(74) *Attorney, Agent, or Firm* — Nixon & Vanderhye P.C.

(57) ABSTRACT

A mask system for use between a patient and a device to deliver a breathable gas to the patient includes a frame including a channel and a cushion provided to the frame. The cushion includes an end portion that is inserted and retained within the channel. The frame includes a recess that communicates with the channel and a hole that connects the recess to a frame exterior. The hole and recess provide an exit route for air contained within the channel.

12 Claims, 22 Drawing Sheets

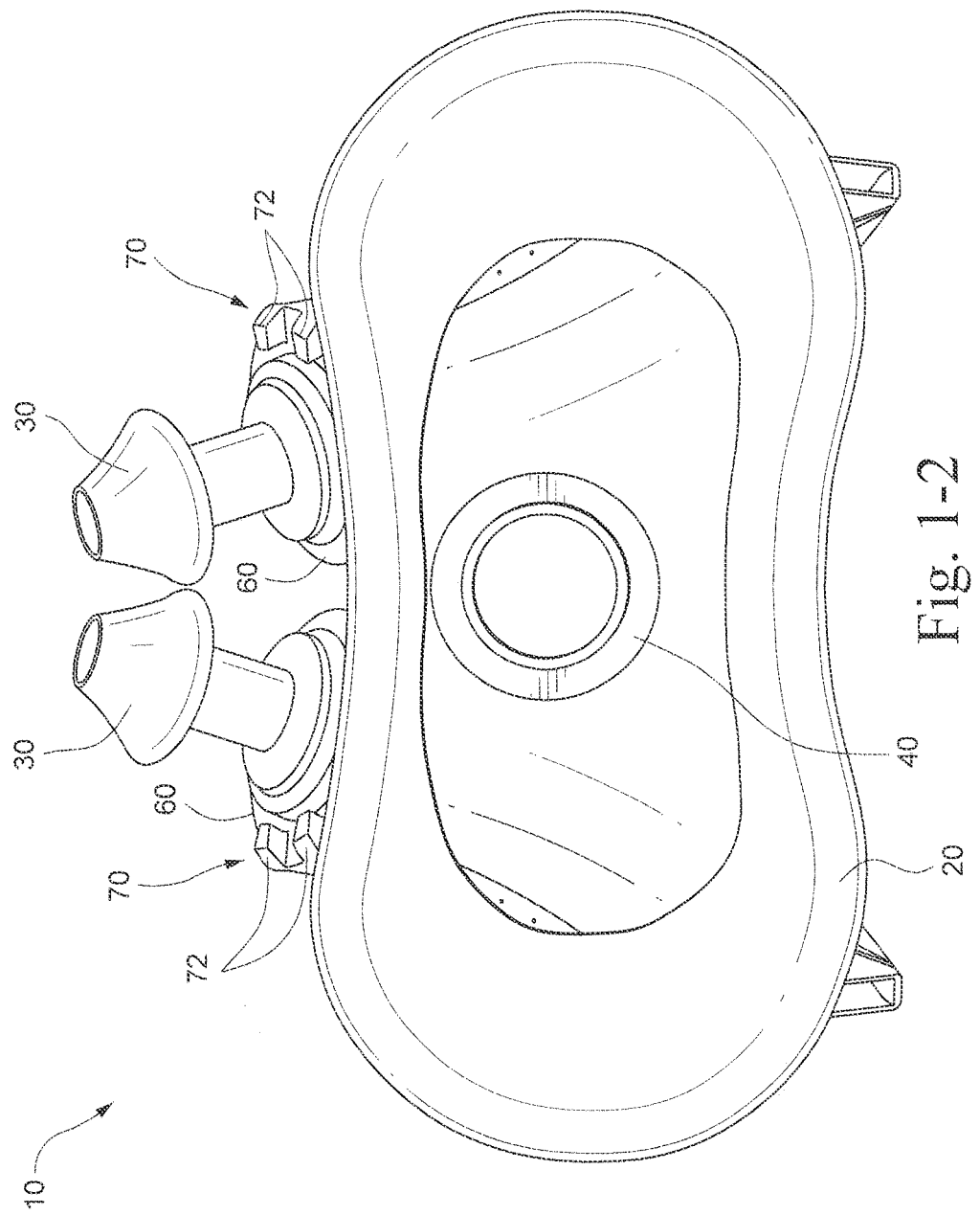

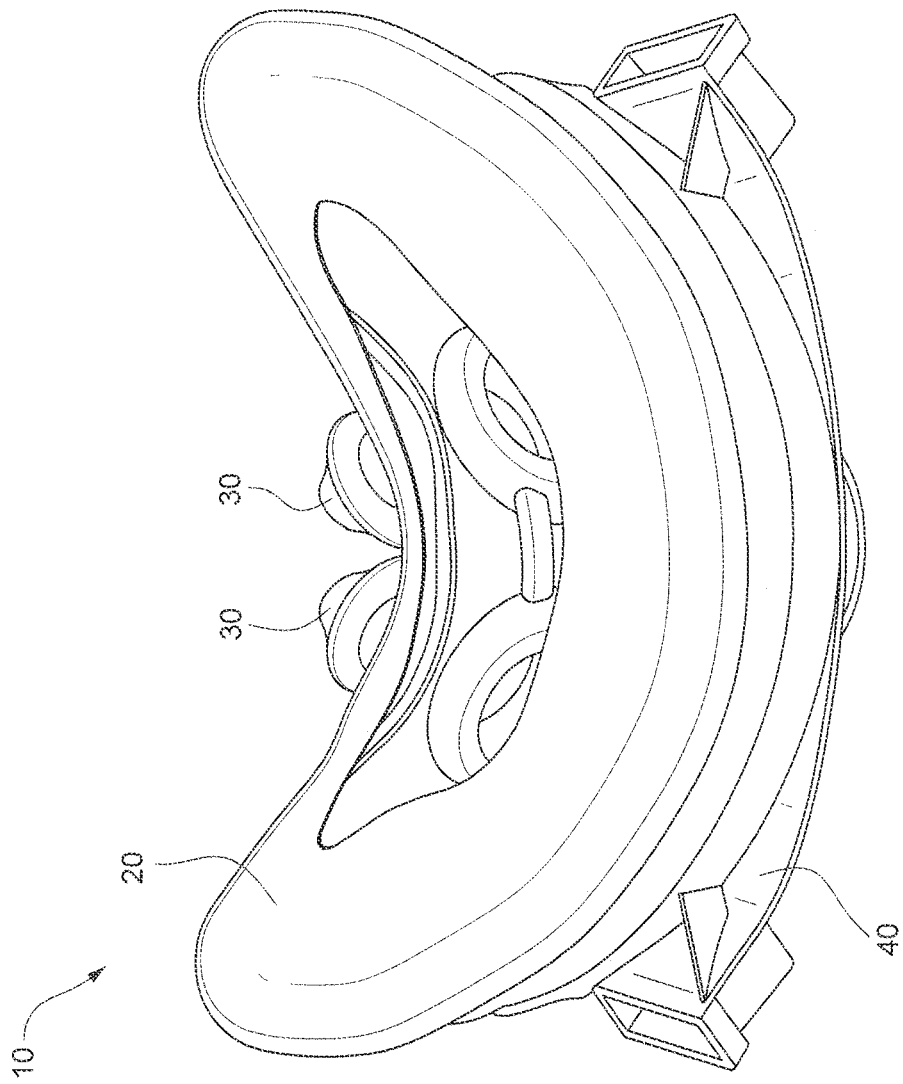

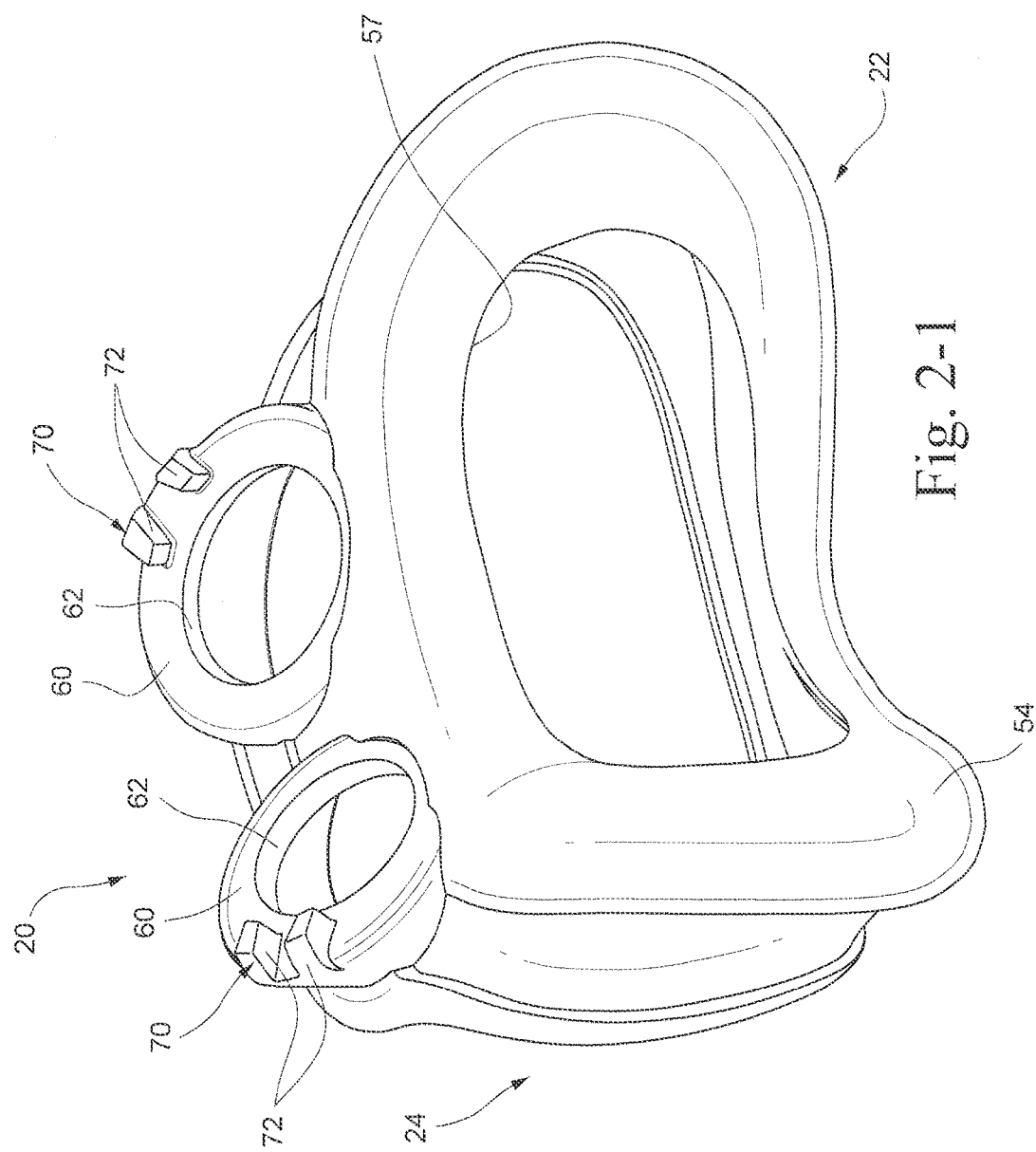

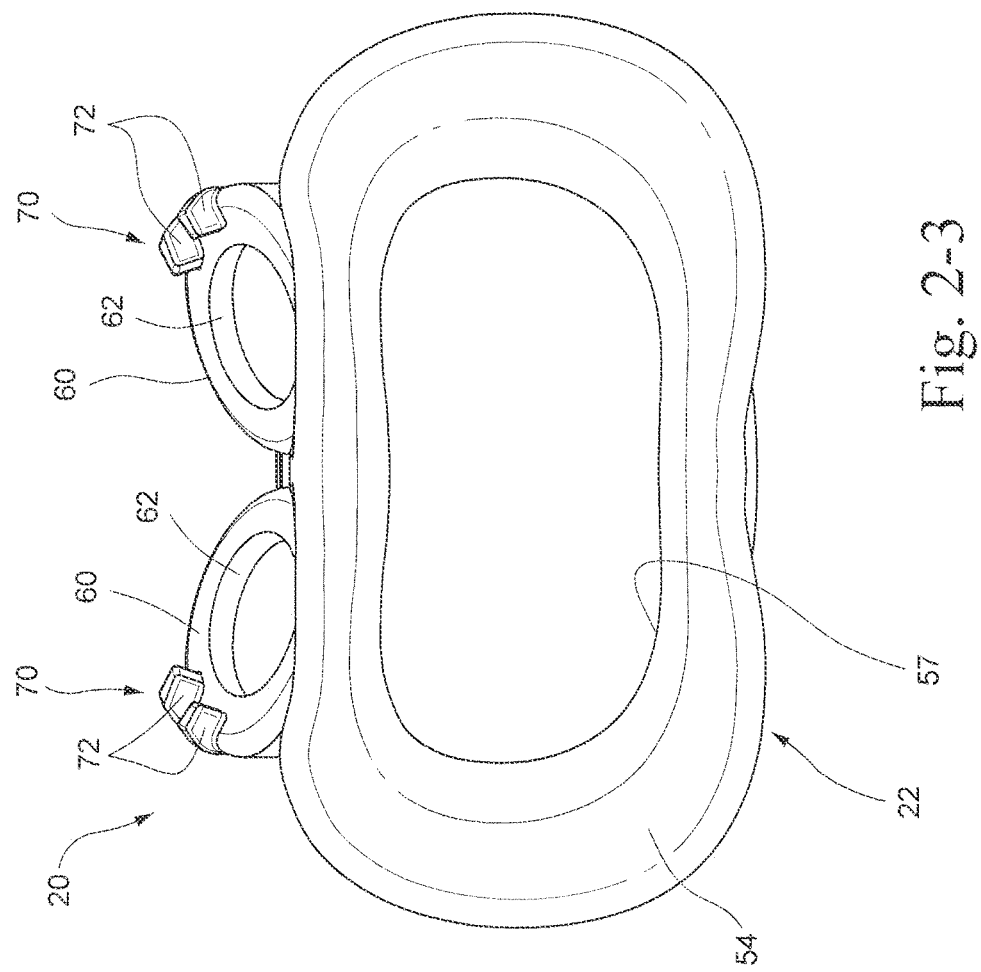

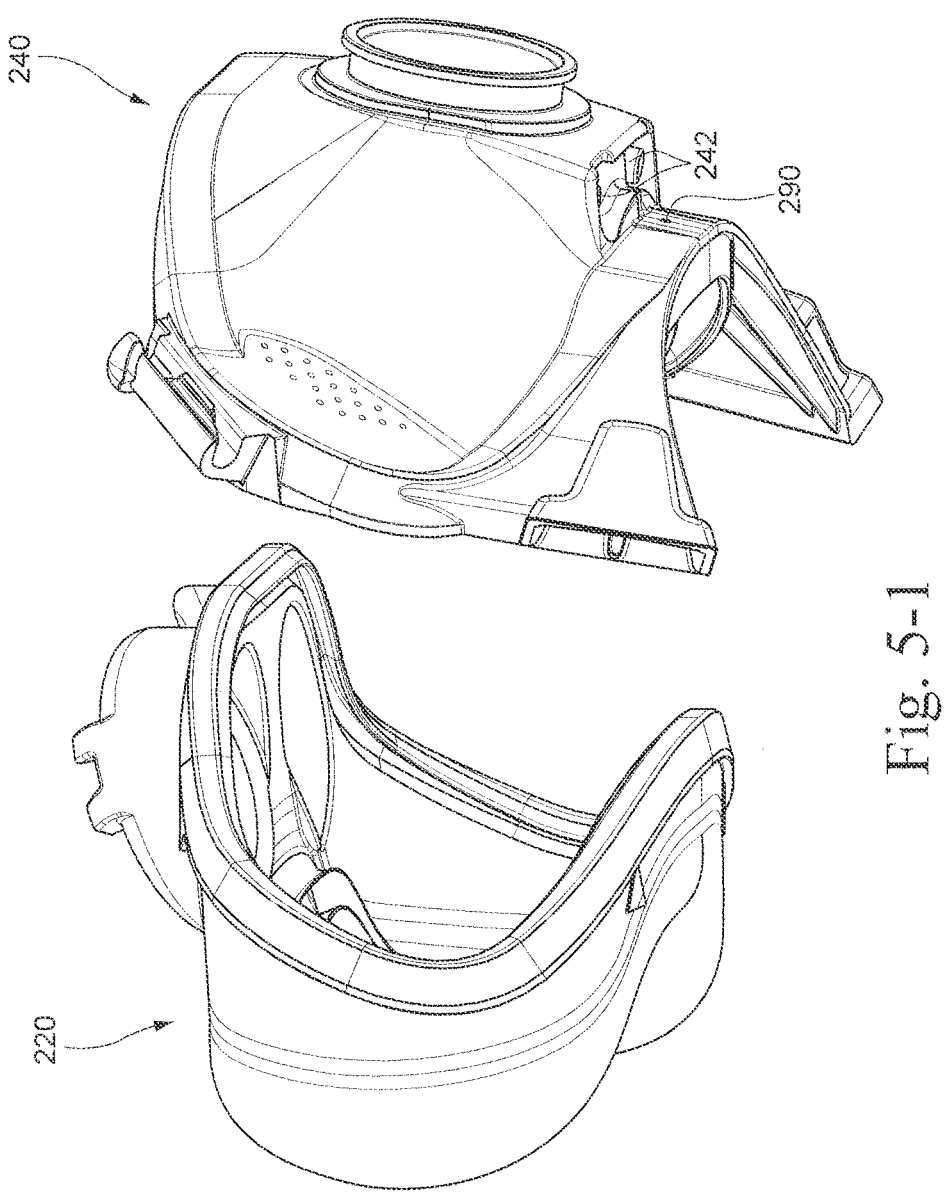

CUSHION FOR MASK SYSTEM

CROSS-REFERENCE TO APPLICATIONS

This application is a continuation of U.S. patent application Ser. No. 12/311,489, filed Jan. 15, 2010, allowed, which is the U.S. National Phase of International Application No. PCT/AU2007/001456, filed Oct. 2, 2007, which designated the U.S. and claims the benefit of U.S. Provisional Application No. 60/848,360, filed Oct. 2, 2006, each of which is incorporated herein by reference in its entirety.

Also, PCT Application No. PCT/AU2006/000770, filed Jun. 6, 2006, and U.S. application Ser. No. 11/447,295, filed Jun. 6, 2006, are each incorporated herein by reference in its entirety.

FIELD OF THE INVENTION

The present invention relates to a cushion for a mask system used for treatment, e.g., of Sleep Disordered Breathing (SDB) with Continuous Positive Airway Pressure (CPAP) or Non-Invasive Positive Pressure Ventilation (NIPPY).

BACKGROUND OF THE INVENTION

Mask systems form an interface between a patient and apparatus providing a supply of pressurized air or breathing gas and are hence sometimes referred to as patient interfaces. In this specification, the words mask system and patient interface may be used interchangeably. Mask systems in the field of the invention differ from mask systems used in other applications such as aviation and safety in particular because of their emphasis on comfort. This high level of comfort is desired because patients must sleep wearing the masks for hours, possibly each night for the rest of their lives. Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. Mask systems often include a mechanism for connecting an air delivery conduit. The air delivery conduit is usually connected to a blower or flow generator.

A range of patient interfaces are known including nasal masks, nose & mouth masks, full face masks and nasal prongs, pillows, nozzles & cannulae. Masks typically cover more of the face than nasal prongs, pillows, nozzles and cannulae. In this specification, all will be collectively referred to as patient interfaces or mask systems. Nasal prongs, nasal pillows, nozzles and cannulae all will be collectively referred to as nasal prongs.

An inherent characteristic of nasal masks is that they do not seal the mouth region. A number of patients thus find that during sleep when muscles relax, mouth leak may occur. Alternatively, some patients are naturally mouth breathers and thus find a nasal mask type patient interface ineffective. Mouth leak is undesirable as, among other difficulties, it may result in noise, increased treatment pressure to compensate for the leak or an increased load on the nasal passages and potentially nasal obstruction or a runny nose. Full face masks or nose & mouth masks address this issue by sealing around both the nose and the mouth.

Leak is a problem common to all designs of patient interface. Since nasal bridge anthropometry varies greatly between patients, the soft patient contacting portion or cushion must adapt to the shapes of individual patients. Typically, this is not achieved for the entire range of patients and some form of leak occurs. The problem is heightened during sleep when the jaw moves and the head position changes. This action can often serve to dislodge the mask and cause leak. Since leak can be noisy and results in less-effective treatment, users often compensate by tightening the headgear more than is desired. This is detrimental for patient comfort and can cause skin breakdown or irritation.

A further problem encountered by patients who are using full face, nasal or nose and mouth masks is that the portion of the patient interface that seals around the nasal bridge prevents the patient from wearing spectacles. Additionally, it may give the sensation of being closed in, leading to a feeling of claustrophobia, particularly when combined with a mouth-sealing portion. A further disadvantage is that any leaks that may occur can affect the sensitive area surrounding the eyes.

Thus, there is a need for an improved mask system that does not suffer from the above-mentioned drawbacks.

SUMMARY OF THE INVENTION

One aspect of the present invention relates to a mouth cushion for a mask system. The mouth cushion includes a side wall, an undercushion extending away from the side wall, and a membrane provided to substantially surround the undercushion and adapted to form a continuous seal around an exterior of a patient's mouth in use. The side wall includes spaced-apart prong support structures that provide annular recesses adapted to support respective nasal prongs. Each prong support structure includes an alignment indicator to aid correct assembly of the respective nasal prong.

Another aspect of the present invention relates to a mouth cushion for a mask system. The mouth cushion includes a side wall, an undercushion extending away from the side wall, and a membrane provided to substantially surround the undercushion and adapted to form a continuous seal around an exterior of a patient's mouth in use. The side wall includes spaced-apart prong support structures that provide annular recesses adapted to support respective nasal prongs. Each prong support structure may includes an alignment indicator to aid correct assembly of the respective nasal prong. At least a portion of the undercushion includes a question-mark or sickle-shape configuration when in cross-section.

Another aspect of the present invention relates to a mask system for use between a patient and a device to deliver a breathable gas to the patient. The mask system includes a frame including a channel and a cushion provided to the frame. The cushion includes an end portion that is inserted and retained within the channel. The frame includes a recess that communicates with the channel and a hole that connects the recess to a frame exterior. The hole and recess provide an exit route for air contained within the channel.

Another aspect of the present invention relates to a nasal prong arrangement for a mask system. The nasal prong arrangement includes a pair of nasal prongs structured to sealingly communicate with nasal passages of the patient's nose in use. Each of the nasal prongs is adapted to be assembled to a support structure. Each of the nasal prongs includes at least one marking and/or tab that is adapted to aid alignment of each nasal prong with the support structure.

Another aspect of the present invention relates to a method for assembling a nasal prong to a cushion. The method includes assembling the nasal prong to a support structure provided to the cushion, and aligning a marking and/or tab provided to the nasal prong with an alignment indicator provided to the support structure.

Another aspect of the present invention relates to a mouth cushion for a mask system. The mouth cushion includes a side wall, an undercushion extending away from the side wall, and a membrane provided to substantially surround the undercushion and adapted to form a continuous seal around an exterior of a patient's mouth in use. The side wall includes spaced-apart prong support structures that provide annular recesses adapted to support respective nasal prongs. At least a portion of the undercushion includes structure to encourage bending in use.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-7 illustrate various views of the cushion of the sealing assembly shown in FIGS. 1-1 to 1-3 according to an embodiment of the present invention;

FIGS. 3-1 to 3-2 illustrate various views of a frame of the sealing assembly shown in FIGS. 1-1 to 1-3;

FIGS. 4-1 to 4-3 illustrate various views of a cushion according to another embodiment of the present invention;

FIGS. 5-1 to 5-4 illustrate various views of assembling a cushion to a frame according to an embodiment of the present invention;

FIGS. 6-1 to 6-3 illustrate various views of a sealing assembly for a mask system including a cushion according to another embodiment of the present invention;

FIG. 7-1 is a perspective view of a paired prong arrangement according to an embodiment of the present invention;

FIG. 7-2 is a top view of a mask system illustrating the paired prong arrangement shown in FIG. 7-1 assembled to a cushion according to an embodiment of the present invention;

FIG. 8-1 is a cross-sectional view of a cushion according to another embodiment of the present invention;

FIG. 9-1 is a cross-sectional view of a cushion according to another embodiment of the present invention;

FIG. 9-2 is a schematic view of a cushion illustrating cross-sectional configuration around its circumference according to an embodiment of the present invention; and FIG. 9-3 is a schematic view of a cushion illustrating cross-sectional configuration around its circumference according to another embodiment of the present invention.

DETAILED DESCRIPTION OF ILLUSTRATED EMBODIMENTS

Each illustrated embodiment includes features that may be used with the embodiments and/or components described in PCT Application No. PCT/AU2006/000770, filed Jun. 6, 2006, and U.S. application Ser. No. 11/447,295, filed Jun. 6, 2006, as would be apparent to those of ordinary skill in the art. PCT Application No. PCT/AU2006/000770 and U.S. application Ser. No. 11/447,295 are each incorporated herein by reference in its entirety.

The following illustrates several alternative embodiments of the present invention, which may share common characteristics and features. It is to be understood that one or more features of any one embodiment may be combinable with one or more features of the other embodiments. In addition, each single feature or combination of features in any of the embodiments may constitute an additional embodiment.

1. Sealing Assembly

Figure 1:
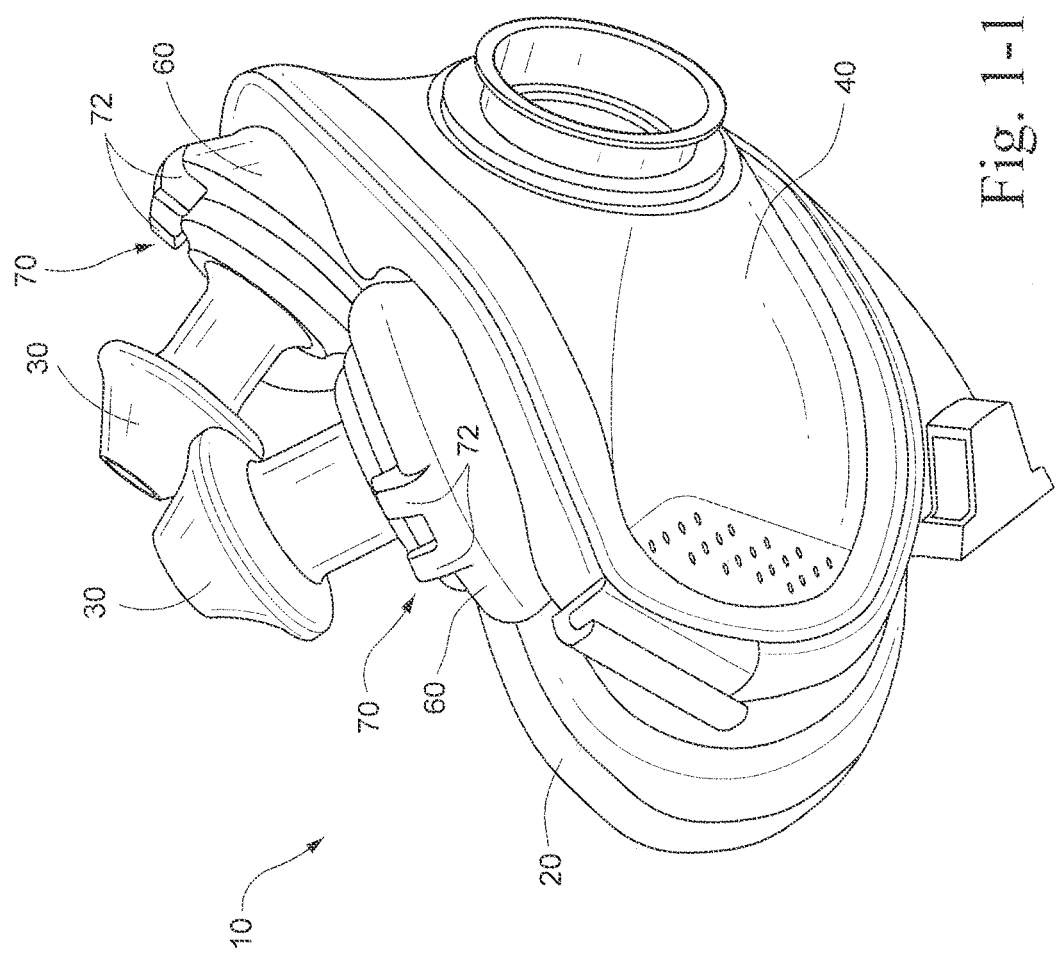
FIGS. 1-1 to 1-3 illustrate various views of a sealing assembly for a mask system including a cushion according to an embodiment of the present invention.
Figure 2:
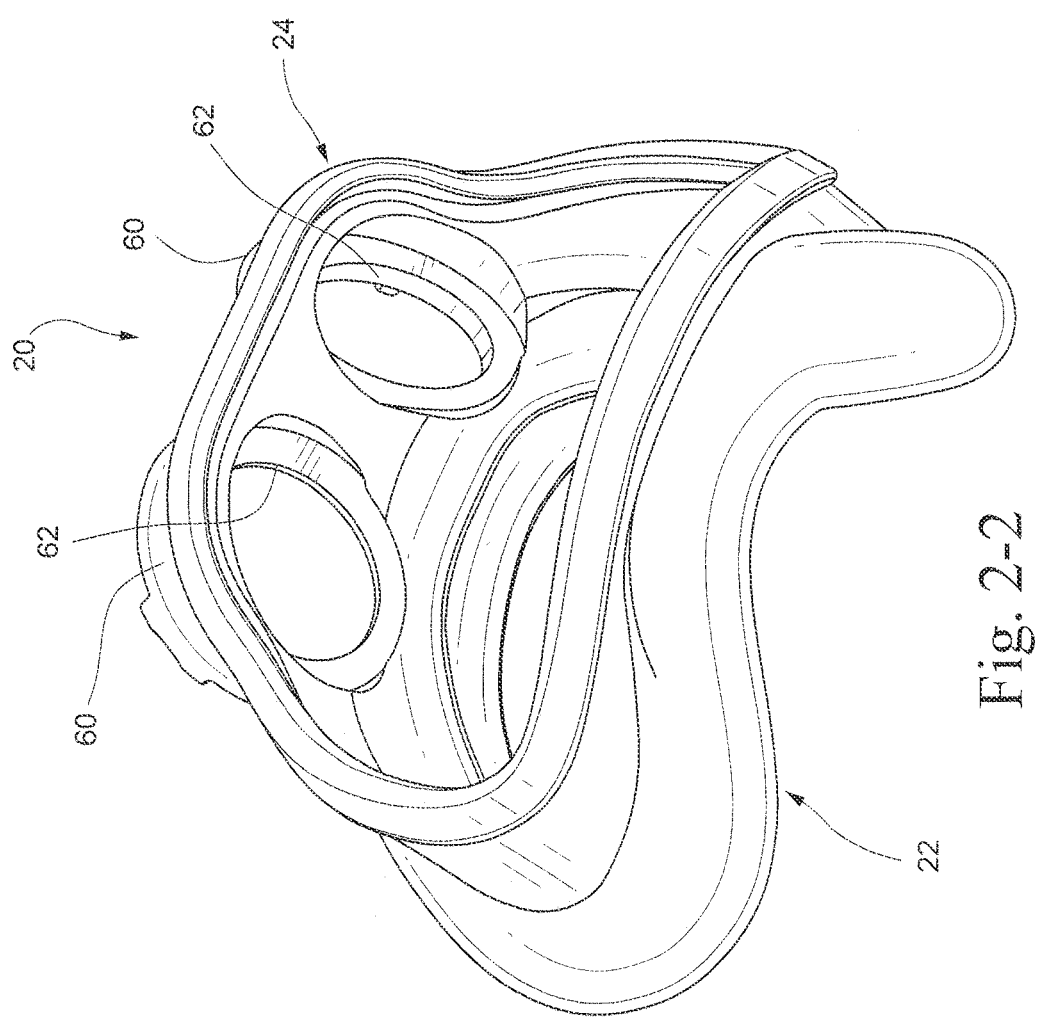
Figures 2, 3, 4:
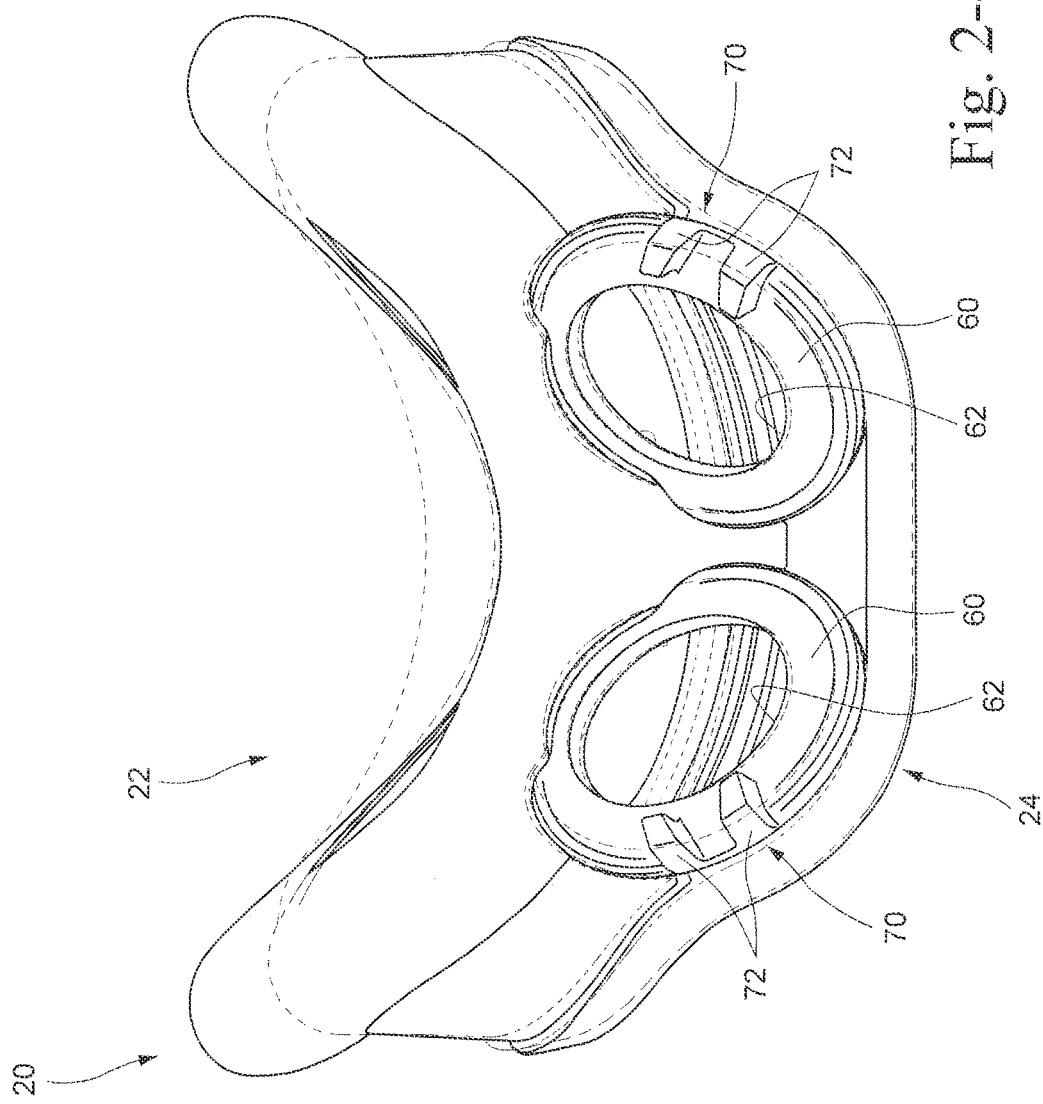

FIGS. 1-1 to 1-3 illustrate a sealing assembly 10 for a mask system that includes a cushion 20 according to an embodiment of the present invention. The sealing assembly 10 is structured to provide an effective seal with both the patient's mouth and the patient's nasal passages in use. The sealing assembly 10 is adapted to be coupled to an elbow assembly, e.g., swivel elbow, that delivers breathable gas to the patient, and a headgear assembly that maintains the sealing assembly 10 in a desired position on the patient's face.

The sealing assembly 10 includes a mouth cushion 20 structured to sealingly engage around an exterior of a patient's mouth in use and a pair of nasal prongs 30 structured to sealingly communicate with the nasal passages of the patient's nose in use. The cushion 20 is structured to be removably and replaceably attached to a substantially rigid frame 40 (see FIGS. 3-1 and 3-2).

Further details and embodiments of this type of mask system including further details and embodiments of nasal prongs and frames are disclosed in the above noted PCT Application No. PCT/AU2006/000770 and U.S. application Ser. No. 11/447,295.

1.1 First Embodiment of Mouth Cushion

FIGS. 2-1 to 2-7 illustrate the mouth cushion 20 of the sealing assembly according to an embodiment of the present invention. As illustrated, the mouth cushion 20 includes a face-contacting portion 22 and a non-face-contacting portion 24.

As best shown in FIGS. 2-6 and 2-7, the face-contacting portion 22 of the cushion 20 includes a side wall 50, an undercushion 52 extending away from the side wall 50, and a membrane 54 provided to substantially surround the undercushion 52 and provide a sealing structure for the face-contacting portion 22. The inner edge of the membrane 54 defines an aperture 57 that receives the patient's mouth (see FIGS. 2-1 and 2-3).

The non-face-contacting portion 24 is structured to be removably and replaceably attached to the frame 40. As best shown in FIGS. 3-1 and 3-2, the frame 40 includes a main body 44 having a side frame portion 46 on each lateral side thereof. The main body 44 includes an aperture 45 and a flanged collar member 47 adapted to engage an elbow. Also, each side frame portion 46 includes headgear attachment points, e.g., upper and lower anchors 48, 49, for attaching a headgear assembly. Such a frame arrangement is disclosed in the above noted PCT Application No. PCT/AU2006/000770 and U.S. application Ser. No. 11/447,295.

In the illustrated embodiment, the non-face-contacting portion 24 includes an arrow-head type design having a tapered end portion 56 with a sealing lip 58 (see FIGS. 2-6 and 2-7). The tapered end portion 56 is adapted to be easily inserted and retained within a channel provided on the frame 40 in manner as described below.

1.1.1 Alignment Indicators

The side wall 50 of the cushion 20 includes spaced-apart prong support structures 60 that provide annular recesses 62 adapted to support respective prongs 30. As illustrated, the prong support structures 60 provide an angled pedestal that project the prongs 30 at the correct angle to the patient's nares (e.g., see FIGS. 1-1 to 1-2).

Moreover, each prong support structure 60 includes an alignment indicator 70 to aid correct assembly of the respective prong 30. Specifically, each alignment indicator 70 includes spaced-apart tabs or protrusions 72. The spaced-apart tabs 72 protrude from a top wall of the prong support structure 60 adjacent the recess 62. Also, the alignment indicator 70 is provided to a side of the prong support structure 60 that is easy visible, e.g., oriented along the side of the cushion 20.

In use, the alignment indicators 70 provide a visual and tactile feedback system to aid assembly of the prongs 30 to the mouth cushion 20. This arrangement may be particularly helpful since the prongs 30 may be molded straight, e.g., see FIG. 7-1, and then flexed on assembly to the mouth cushion 20.

In an alternative embodiment, each prong 30 may include a marking that is adapted to align with a respective alignment indicator 70. In a further alternative embodiment, each prong 30 may include a tab that is adapted to engage a respective alignment indicator 70 to aid correct assembly. In embodiments, each prong may include multiple markings and/or multiple tabs that allows one of multiple positions or angles of the prong to be selected for assembly.

Figures 2, 3, 4, 5:
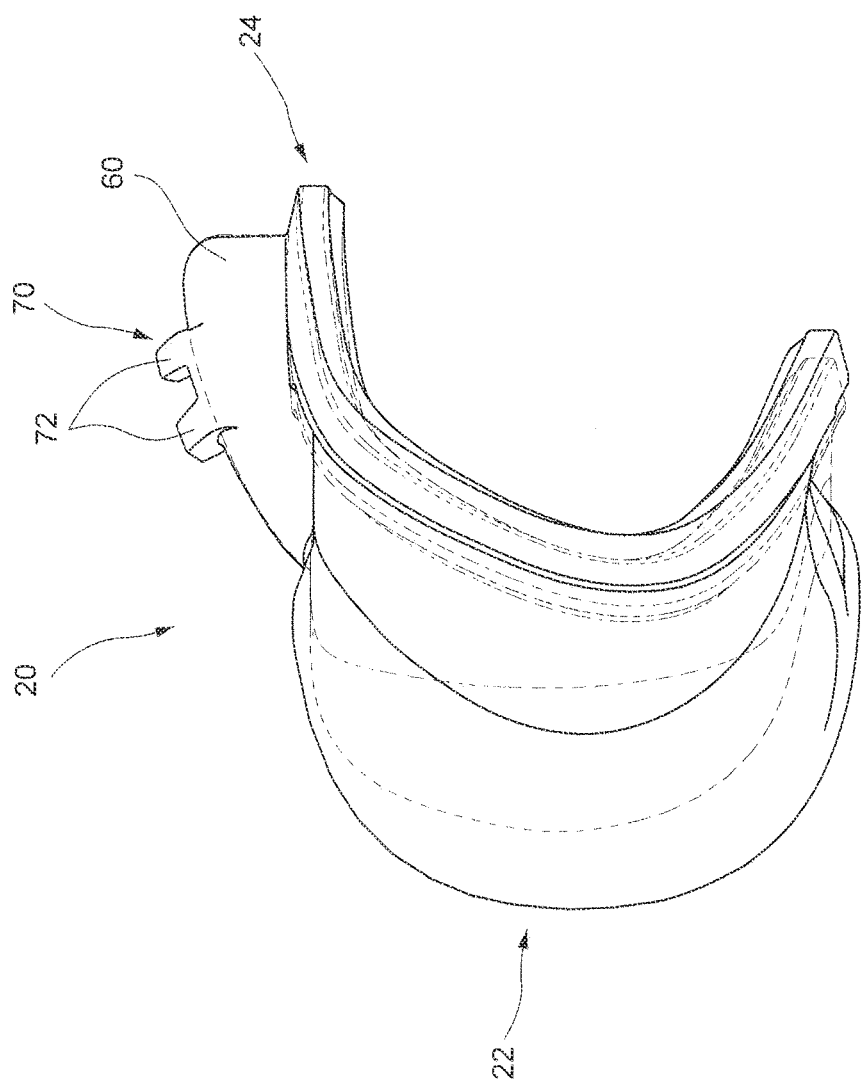
Figures 2, 3, 4, 5, 6:
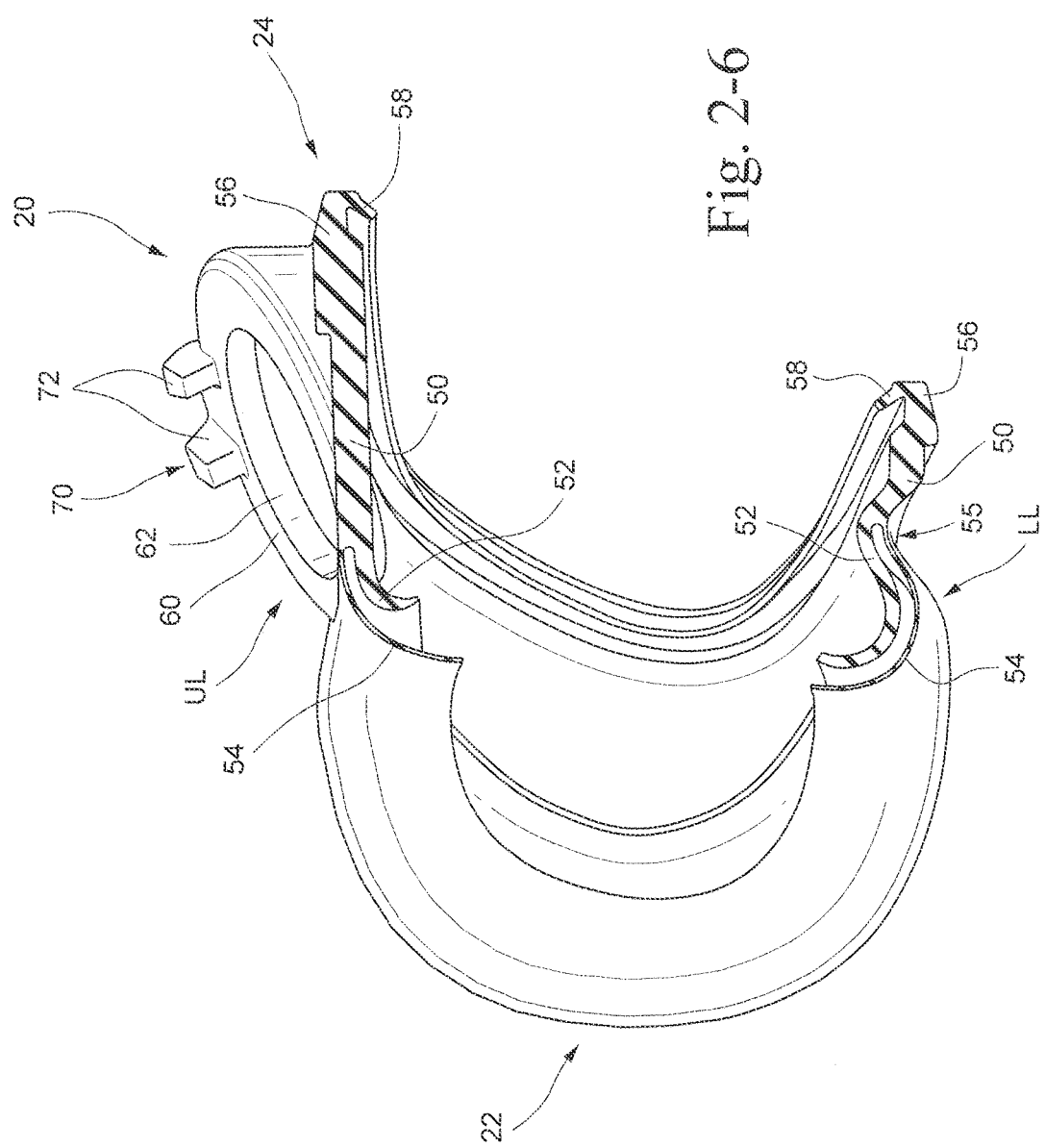
Figures 2, 3, 4, 5, 6, 7:
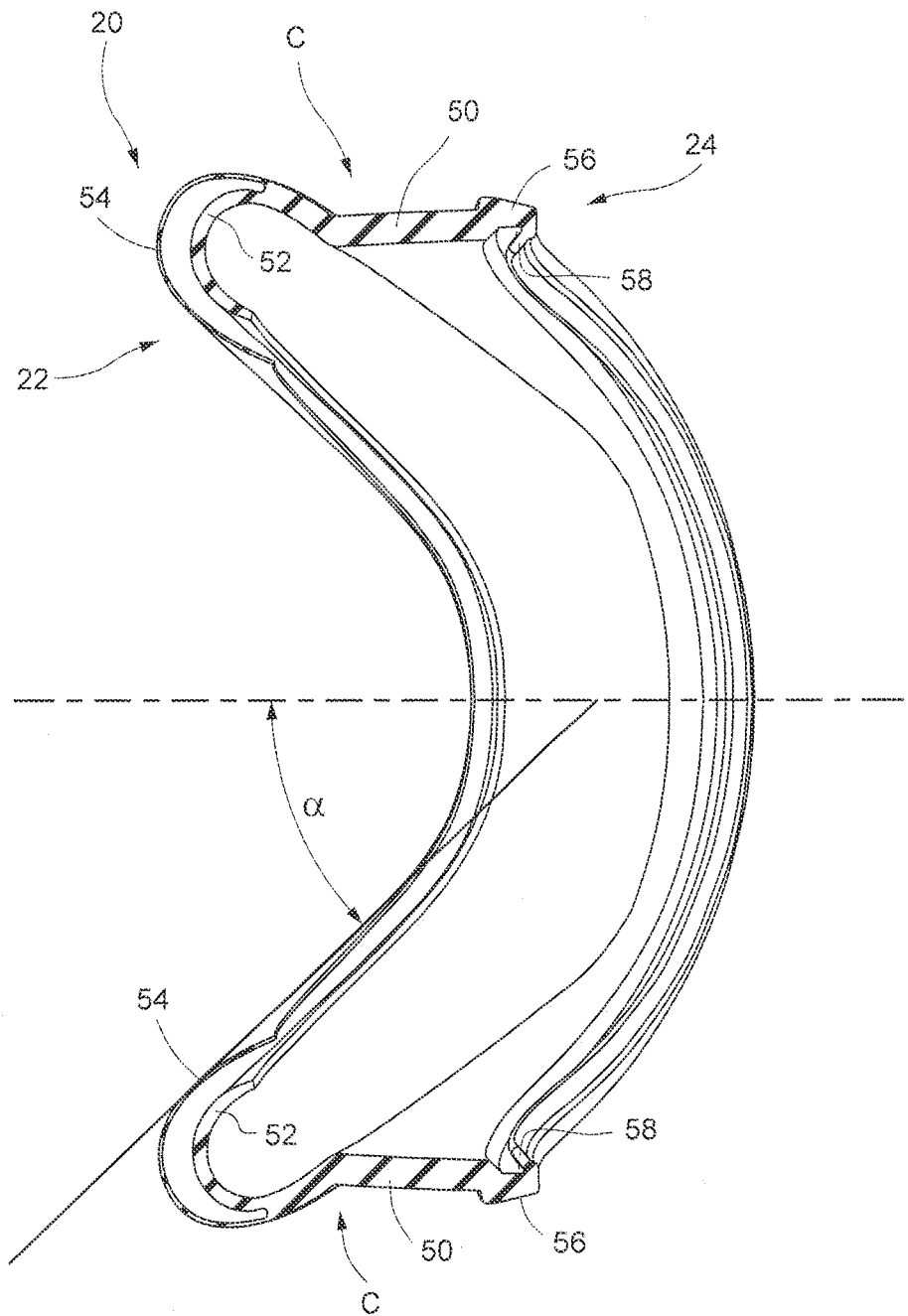
Figures 1, 3:
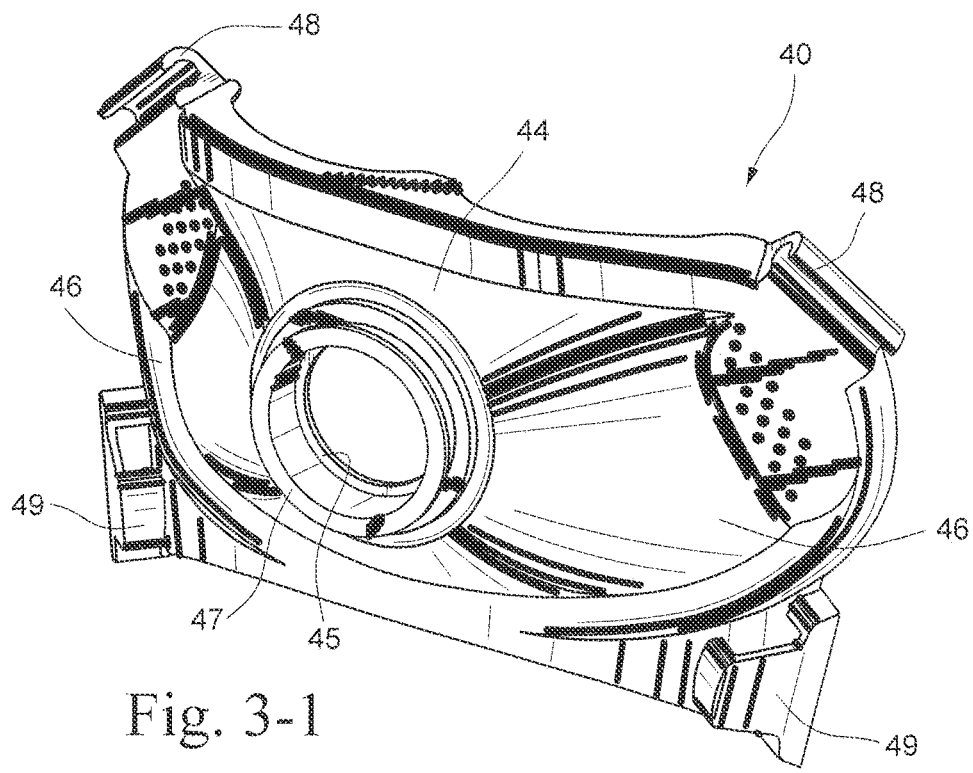
Figures 2, 3:
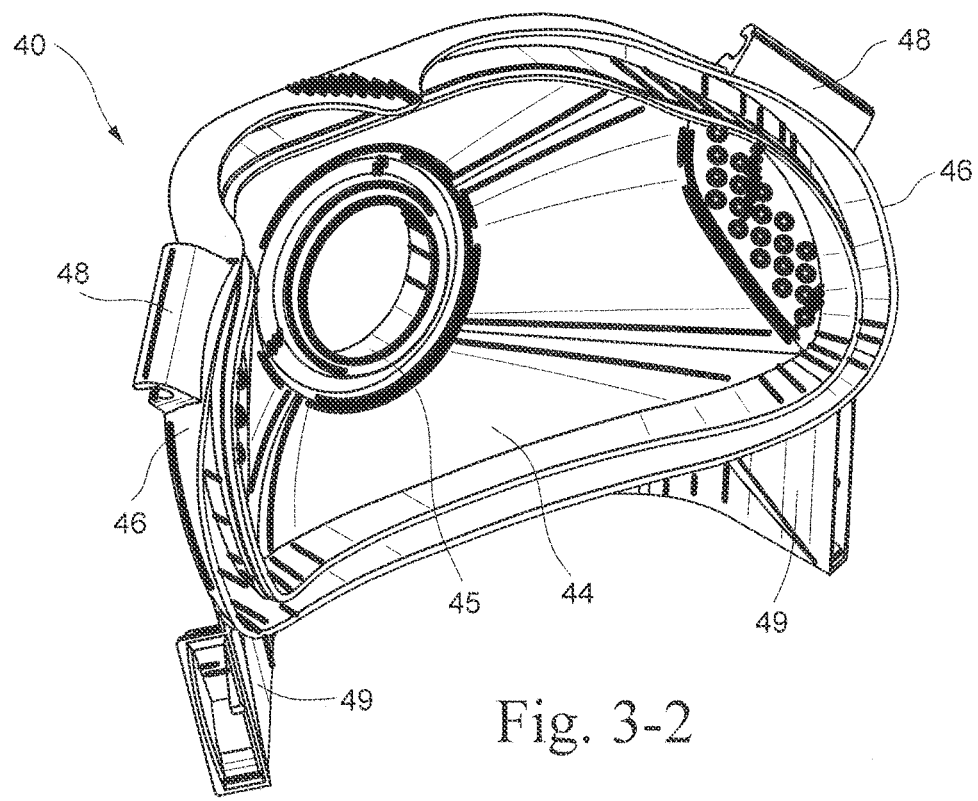
Figures 1, 4:
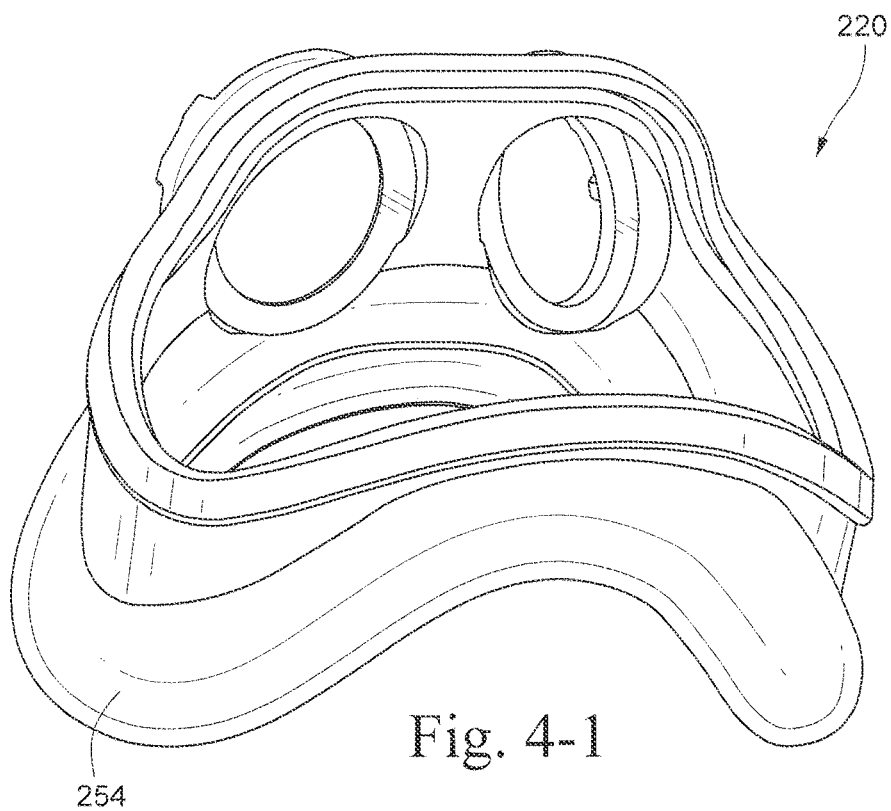
Figures 2, 4:
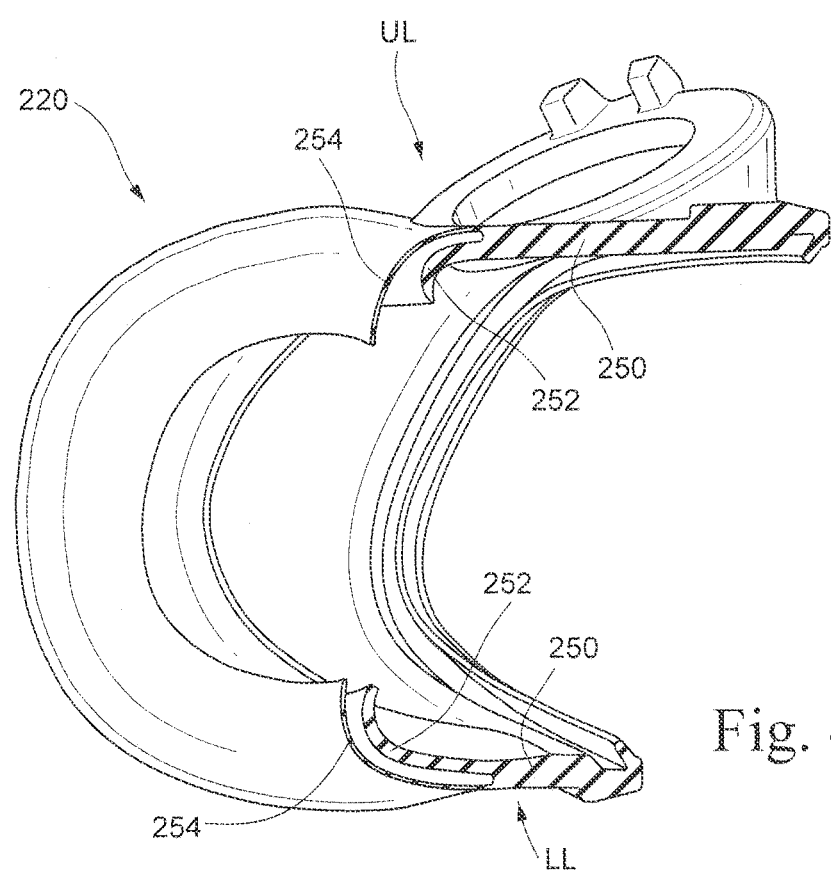
Figures 3, 4:
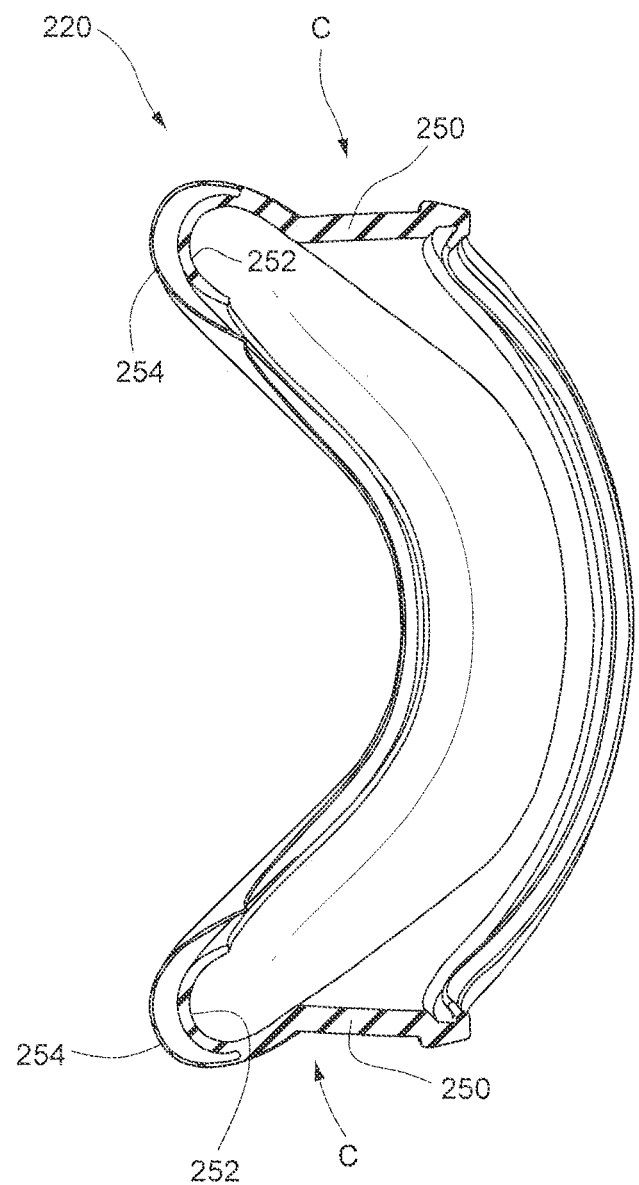
Figures 2, 5:
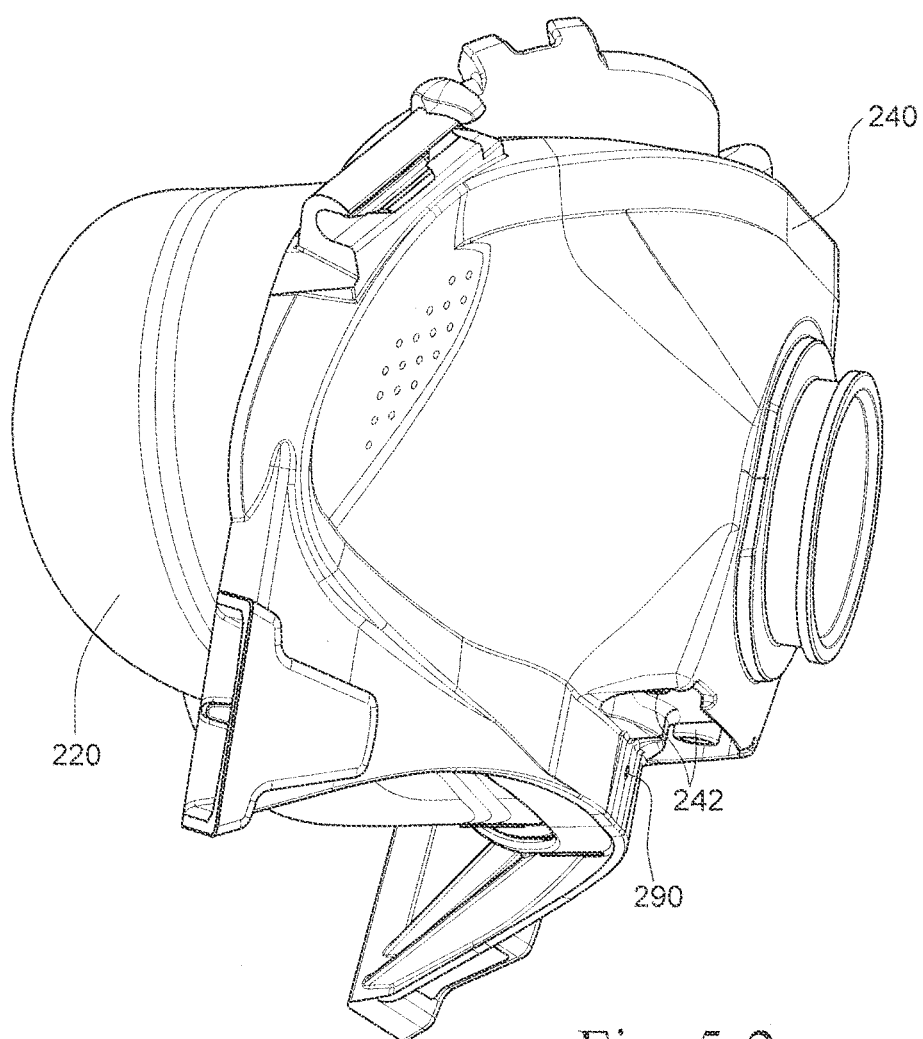
Figures 3, 5:
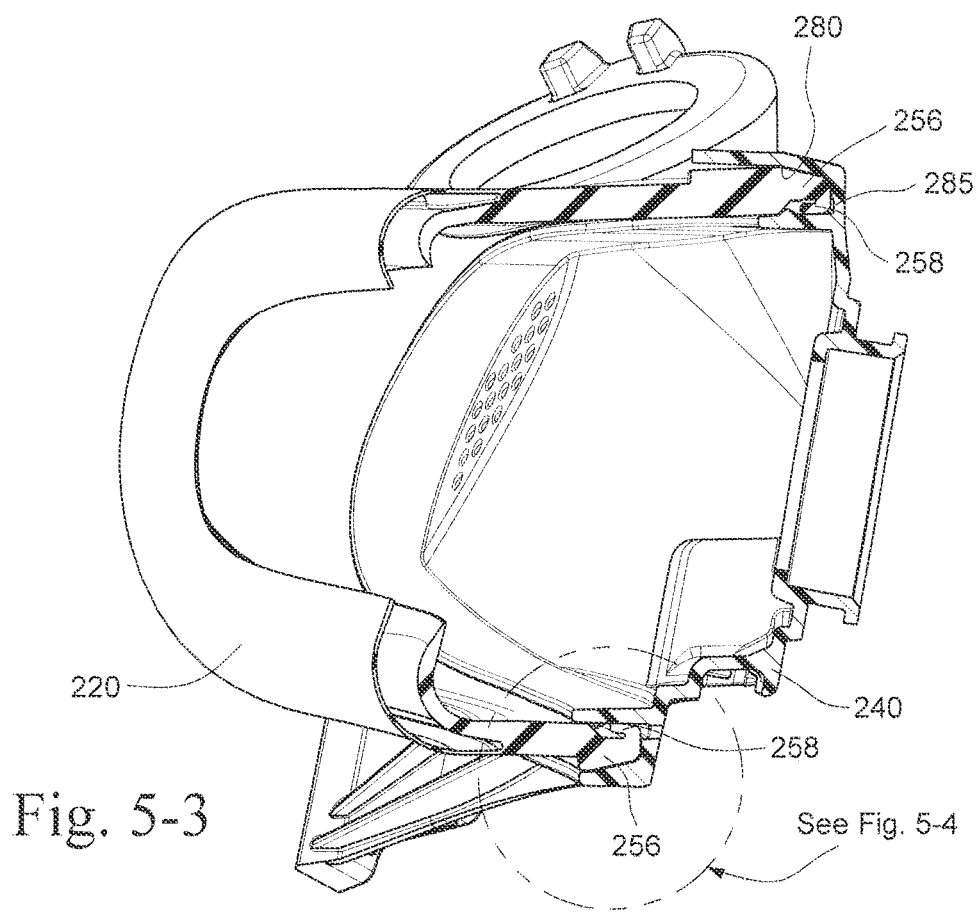
Figures 4, 5:
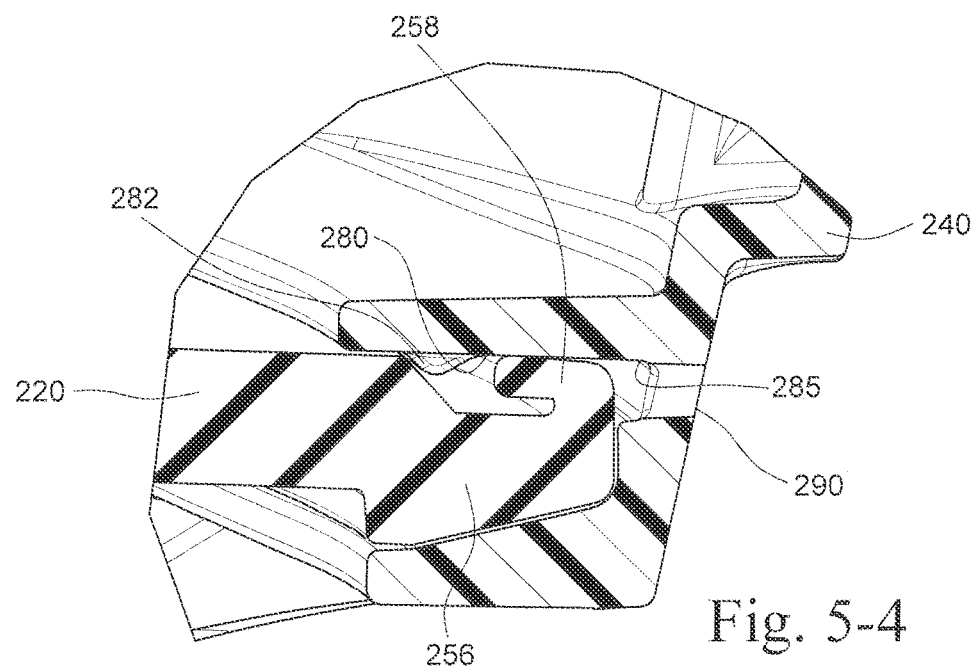
Figures 1, 6:
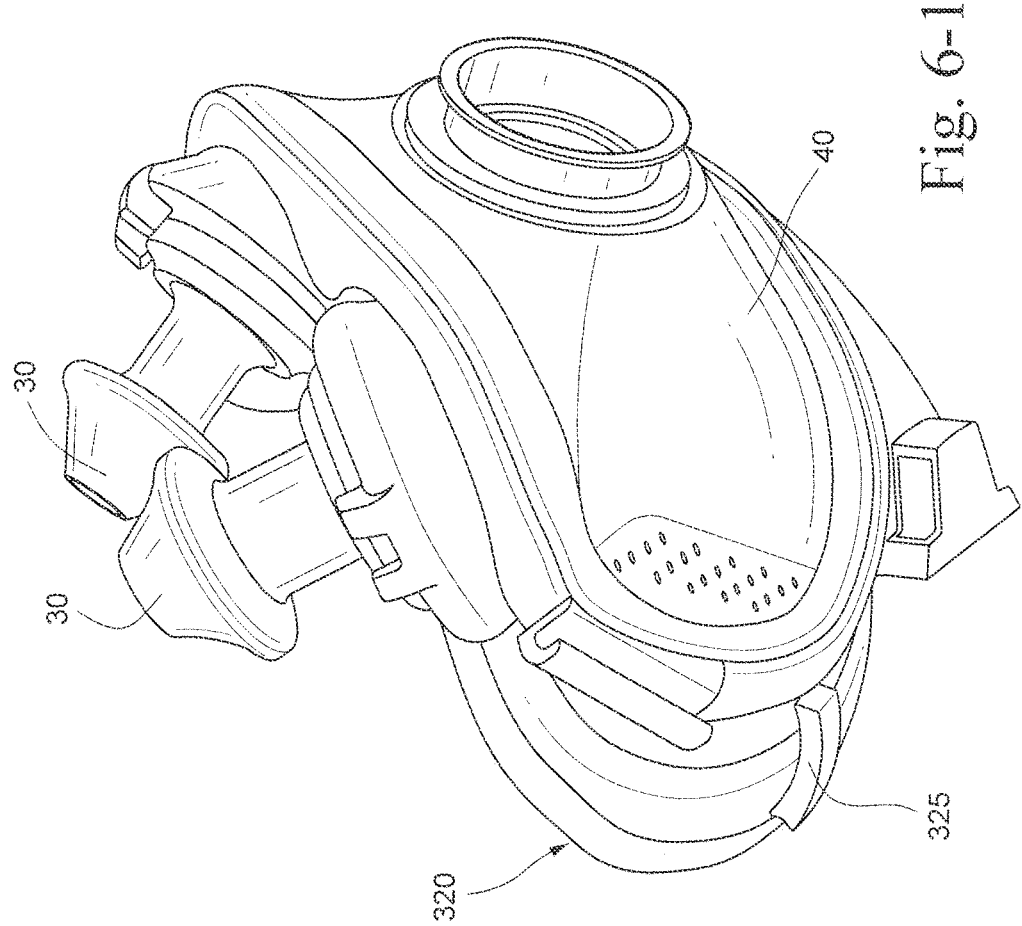
Figures 2, 6:
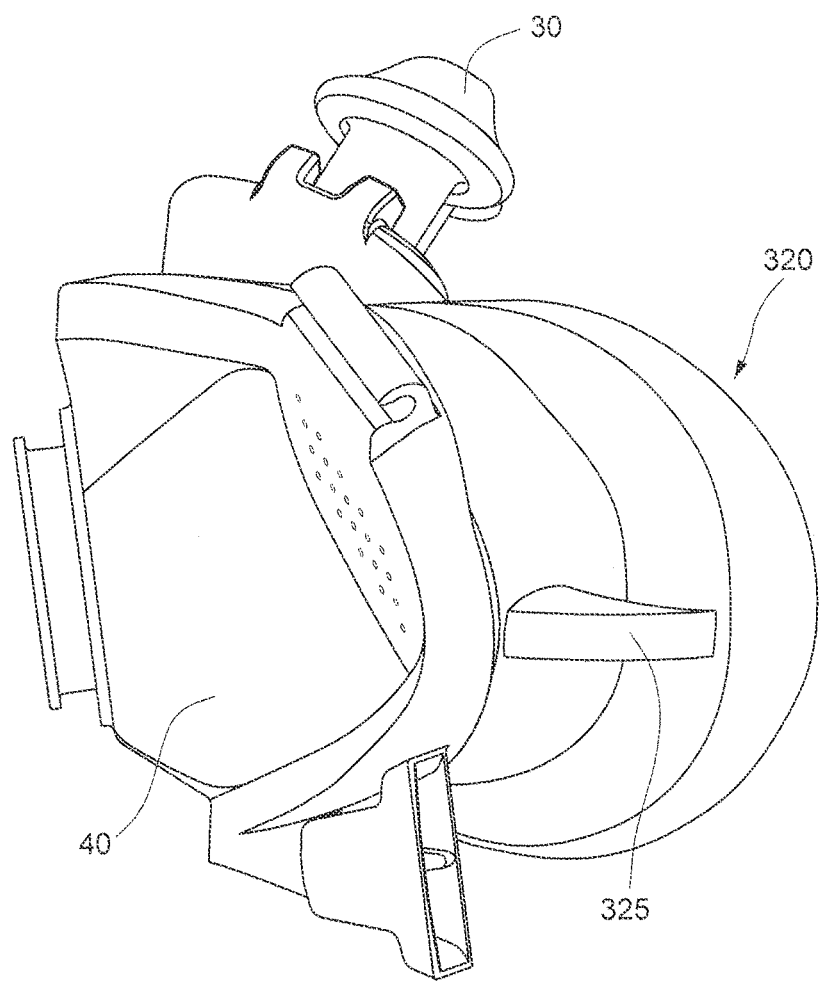
Figures 3, 6:
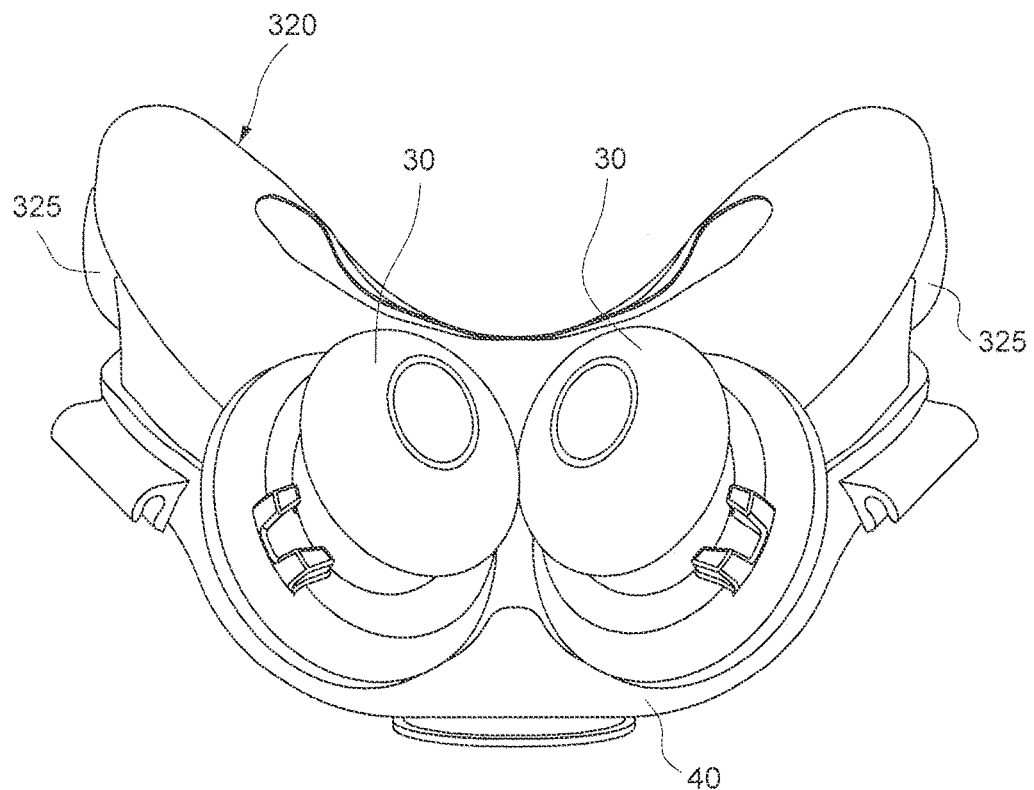
Figures 1, 7:
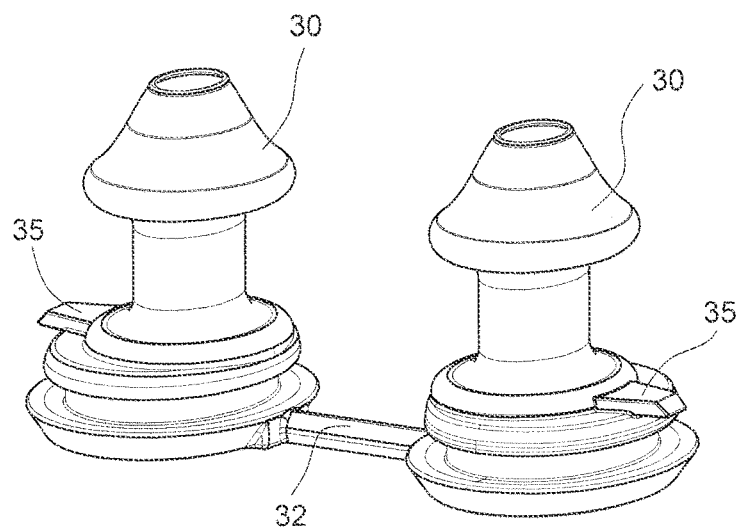
Figures 2, 7:
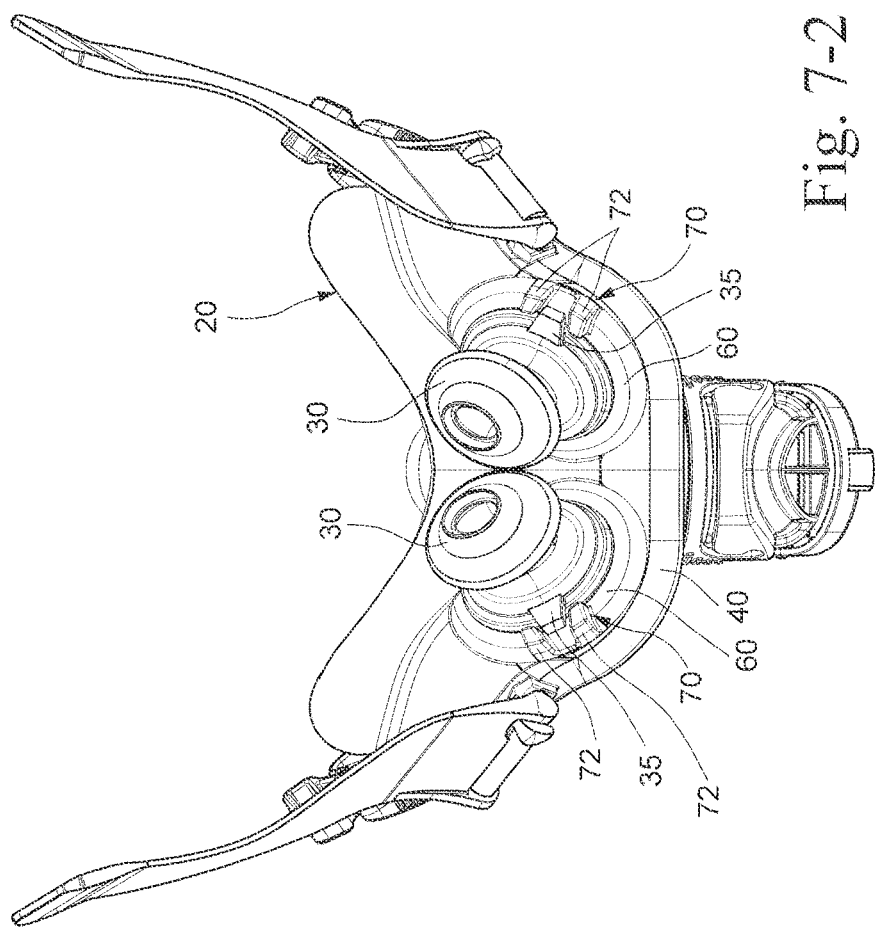

For example, FIG. 7-1 illustrates a paired-prong arrangement including prongs 30 joined by a bridging or connecting strap 32. As illustrated, each prong 30 includes a tab 35 that extends radially outwardly from a base portion thereof. When the paired-prong arrangement is assembled to the cushion 20, as shown in FIG. 7-2, the tab 35 of each prong 30 engages a respective alignment indicator 70 to aid correct assembly, e.g., tab 35 extends between the spaced-apart tabs 72. It should be understood that such a tab arrangement may be provided to a single-prong arrangement that is molded and assembled individually to the cushion 20.

1.1.2 Cushion Profile

The profile of the cushion 20 is structured to provide a better seal and may include characteristics and/or features similar to the cushion profile disclosed in PCT/AU2006/000032, filed Jan. 12, 2006, which is incorporated herein by reference in its entirety.

FIG. 2-6 illustrates a cross-section of the cushion 20 between the prong support structures 60. As illustrated, at the upper lip section UL of the cushion profile, the side wall 50, undercushion 52, and membrane 54 are all generally aligned in a relatively straight profile. However, at the lower lip section LL of the cushion profile, the lower portion of the undercushion 52 has a more arcuate, e.g., semi-circular, question-mark, sickle-shape, configuration that defines a space 55 below a lower portion of the undercushion 52 and adjacent the side wall 50. This arcuate configuration provides greater flexibility or range of movement to the undercushion 52 in use.

That is, the arcuate configuration provides a spring structure that encourages the cushion wall to resiliently bend rather than buckle. It should be appreciated that the cushion wall may have other suitable configurations to achieve this spring structure or flexibility, e.g., arcuate configuration, varying wall thickness, bellows arrangement, etc.

Moreover, this cushion profile provides a seal that accommodates a wide range of facial profiles, facilitates set-up and achievement of a seal, and accommodates movement of the patient's face during use.

The arcuate configuration is also provided at the sides of the cushion 20, i.e., in the cheek sections C, as shown in FIG. 2-7. In addition, the cushion 20 may be designed at an angle α steeper than the majority of facial profiles to provide an initial contact on the cheeks of the patient and thus ensure a strong seal at these points. In an embodiment, the angle α in FIG. 2-7 may be in the range of 30-50°, e.g., 40°.

Also, FIGS. 2-4 and 2-5 illustrate the cushion 20 (in solid lines) with respect to a cushion (in dashed lines) disclosed in the above noted PCT Application No. PCT/AU2006/000770 and U.S. application Ser. No. 11/447,295.

1.2 Second Embodiment of Mouth Cushion

FIGS. 4-1 to 4-3 illustrate a cushion 220 according to another embodiment of the present invention. In this embodiment, no arcuate configuration is provided over a short distance at the upper lip and lower lip sections UL, LL of the cushion profile. The arcuate configuration is provided at the sides of the cushion 220, which then slowly blends to a flat configuration over a short distance at the top and bottom lip sections.

Specifically, as shown in FIG. 4-2, the side wall 250, undercushion 252, and membrane 254 at the upper lip and lower lip sections UL, LL are all generally aligned in a relatively straight profile. As shown in FIG. 4-3, the lower portion of the undercushion 252 at the cheek sections C has a more arcuate, e.g., semi-circular, question-mark, sickle-shape, configuration that provides greater flexibility to the undercushion 252 in use.

The combination of the arcuate configuration at the cheek sections C and a steeper cushion angle previously discussed provide an improved seal and fit of the cushion 220. The arcuate configuration at the cheek sections C of the cushion 220 are typically the first section of the cushion 220 to contact the patient's face and the arcuate configuration at the cheek sections C then deform as required to allow the cushion 220 to be fitted to the upper lip and lower lip sections UL, LL. The last points of contact are thus the more sensitive areas of the patient's face, i.e., the upper lip and lower lip sections UL, LL. The adjustability in the cheek regions C provided by the arcuate configuration allows the patient to finely adjust the cushion 220 to comfortably fit and seal in these sensitive regions of the upper lip and lower lip sections UL, LL while still maintaining a cheek seal without excessive force.

1.3 Cushion Assembly to Frame

FIGS. 5-1 to 5-4 illustrate assembly of a cushion to a frame according to an embodiment of the present invention. In the illustrated embodiment, the cushion is in the form of cushion 220 described above and indicated with similar reference numerals. The frame 240 is similar to frame 40 described above. In contrast, the frame 240 includes two ports 242, e.g., tubular spigots, located in recesses in the base of the frame 240. It should be appreciated that cushion 20 may be attached to frame 240 in a similar manner, and that cushions 20, 220 may be attached to frame 40 in a similar manner.

As illustrated, the tapered end portion 256 is adapted to be easily inserted and retained within a channel 280 provided on the frame 240. The sealing lip 258 provides a seal around the perimeter of the cushion 220 and also in conjunction with the bead 282 (see FIG. 5-4) around the frame channel 280 retains the cushion 220 onto the frame 240.

In addition, a recess 285 is provided to the frame 240 and communicates with the channel 280 that retains the cushion 220, as best shown in FIG. 5-4. The recess 285 forms a smaller channel around the bottom of the channel 280. Also, a hole 290 is provided below the ports 242 which connects the recess or channel 285 to the exterior of the frame 240 (see FIGS. 5-1, 5-2, and 5-4). It should be appreciated that the hole 290 may be located at any position around the channel 280.

In manufacturing assembly, a vacuum is applied around the hole 290 which in turn creates a vacuum around the channel 285 drawing the cushion 220 into the fully seated position. The hole 290 and channel 285 also help standard assembly by allowing an exit route for the air contained within channel 280 and thus leading to less force required to assemble the cushion 220 to the frame 240. In this embodiment, the channel 285 has a tapered hole, e.g., exit diameter about 1.0-1.3 mm, e.g., 1.16 mm. In alternative embodiments, the hole diameter may vary and multiple holes and/or a deeper/varying section channel may be provided.

1.4 Third Embodiment of Mouth Cushion

FIGS. 6-1 to 6-3 illustrate a cushion 320 according to another embodiment of the present invention. In this embodiment, each side of the cushion 330 includes a support strut or rib 325. As illustrated, the support strut 325 extends generally horizontally along an exterior surface of the respective side of the cushion 320. In use, the support strut 325 may modify the deflection characteristic of the cushion 320. It should be appreciated that the support strut 325 may have other suitable shapes, arrangements, and positioning along the cushion 320 to modify the deflection characteristic. In addition, one or more support struts may be provided to modify the deflection characteristic.

1.5 Alternative Embodiments of Mouth Cushion

Figures 1, 8:
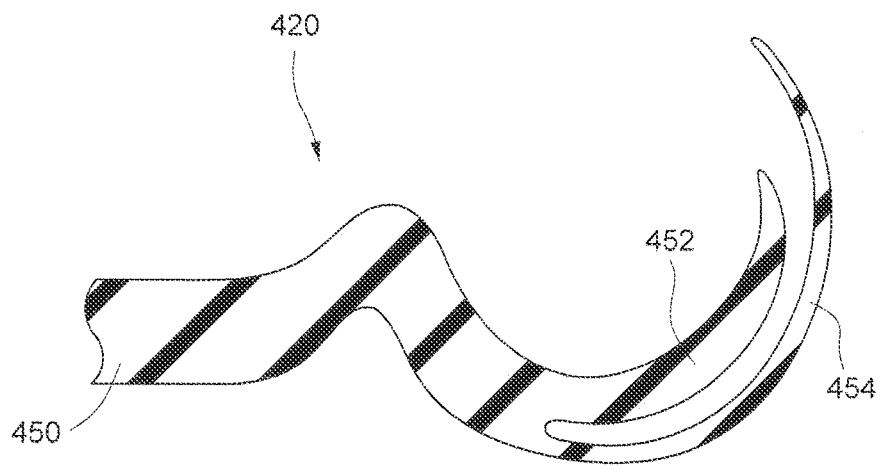

FIG. 8-1 illustrates a cross-section of a mouth cushion 420 according to an alterative embodiment of the present invention. As illustrated, the cushion cross-section includes a side wall 450, undercushion 452, and membrane 454. The undercushion 452 has a more arcuate, e.g., semi-circular, question-mark, sickle-shape, configuration (e.g., in the lower lip section) that provides flexibility to the cushion 420 without extending the footprint of the cushion 420. That is, the cushion 420 may retain the same overall height.

Figures 1, 9:
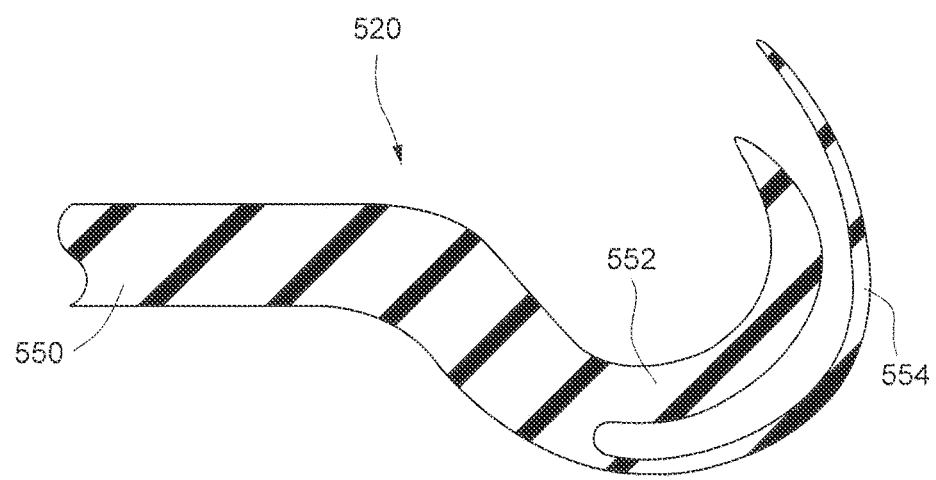
Figures 2, 9:
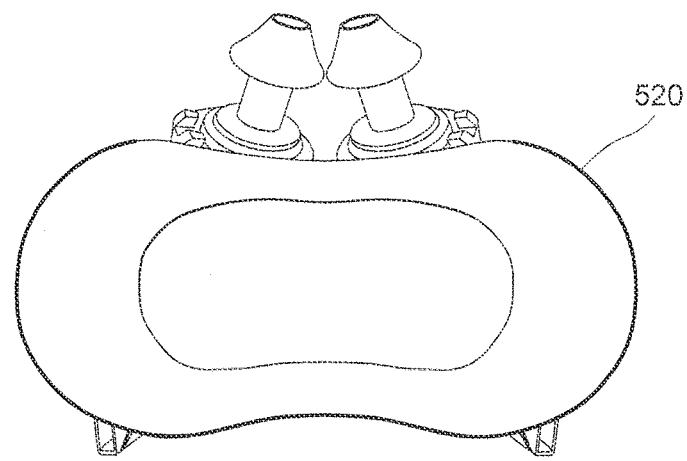
Figures 3, 9:
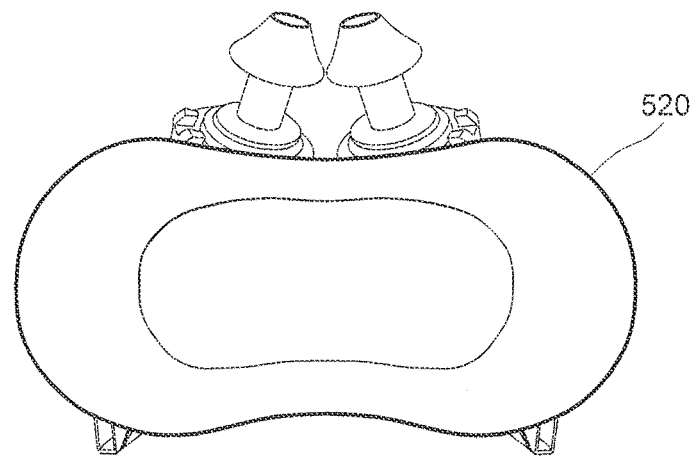

FIG. 9-1 illustrates a cross-section of a mouth cushion 520 according to another alterative embodiment of the present invention. As illustrated, the cushion cross-section includes a side wall 550, undercushion 552, and membrane 554. The undercushion 552 has a more arcuate, e.g., semi-circular, question-mark, sickle-shape, configuration that provides flexibility to the cushion 520.

In an embodiment, the arcuate configuration, e.g., sickle-shaped cross-section, may be provided around a majority of the cushion circumference, as shown in a bold line in FIG. 9-2. Alternatively, the arcuate configuration, e.g., sickle-shaped cross-section, may be provided around the entirety of the cushion circumference, as shown in a bold line in FIG. 9-3. Depending on the radius of curvature of the arcuate shape, this arrangement may have a contact point on the patient's face outside of that which would be achieved with a cushion having a cross-section such as that shown in FIG. 4-2 for example. This allows the frame to be smaller, thereby providing less weight and visually reducing the mask for the patient.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike.

What is claimed is:

1. A mask system for use between a patient and a device to deliver a breathable gas to the patient, the mask system comprising:
    a frame including a channel; and
    a cushion provided to the frame, the cushion including an end portion that is inserted and retained within the channel,
    wherein the frame includes a recess that communicates with the channel and a hole that connects the recess to a frame exterior, the hole and recess providing an exit route for air contained within the channel.

2. The mask system according to claim 1, wherein the end portion is tapered and includes a sealing lip, the tapered end portion adapted to be inserted and retained within a channel.

3. The mask system according to claim 2, wherein the sealing lip provides a seal around the perimeter of the cushion.

4. The mask system according to claim 1, wherein the hole is tapered.

5. The mask system according to claim 1, wherein the hole includes an exit diameter in a range of about 1.0-1.3 mm.

6. The mask system according to claim 1, wherein the frame includes a bead within the channel positioned to interact with the end portion to retain the cushion within the channel.

7. The mask system according to claim 1, wherein the cushion is a mouth cushion adapted to form a seal around an exterior of a patient's mouth.

8. The mask system according to claim 7, wherein the mouth cushion includes a side wall adapted to support a pair of nasal prongs.

9. The mask system according to claim 1, wherein the frame includes a main body having a side frame portion on each lateral side thereof.

10. The mask system according to claim 9, wherein the main body includes an aperture and a flanged collar member adapted to engage an elbow.

11. The mask system according to claim 9, wherein each side frame portion includes a headgear attachment point to attach a headgear assembly.

12. The mask system according to claim 11, wherein each side frame portion includes upper and lower anchors to attach the headgear assembly.

* * * * *